United States Patent [19]
Jensen

[11] Patent Number: 4,468,227
[45] Date of Patent: Aug. 28, 1984

[54] WOUND DRAINAGE DEVICE WITH RESEALABLE ACCESS CAP

[75] Inventor: Marvin E. Jensen, Niles, Ill.

[73] Assignee: Hollister Incorporated, Libertyville, Ill.

[21] Appl. No.: 268,368

[22] Filed: May 29, 1981

[51] Int. Cl.³ .............................................. A61M 1/00
[52] U.S. Cl. ..................................... 604/327; 128/760
[58] Field of Search .............. 128/760, 767, 272, 275, 128/283, 276, 769; 220/306, 375; 215/306, 235, 317, DIG. 1; 150/3; 604/317, 327, 332, 333, 334, 336, 337, 339, 341, 342, 343, 344

[56] References Cited

U.S. PATENT DOCUMENTS

| Re. 29,319 | 7/1977 | Nordby et al. | 128/275 |
|---|---|---|---|
| 2,299,431 | 10/1942 | Shirey | 128/283 |
| 2,367,690 | 1/1945 | Pordy | 128/132 |
| 2,380,740 | 7/1945 | Fenwick | 128/283 |
| 2,928,393 | 3/1960 | Marsan | 128/283 |
| 3,026,874 | 3/1962 | Stevens | 128/260 |
| 3,059,816 | 10/1962 | Goldstein | 215/235 |
| 3,523,534 | 8/1970 | Nolan | 128/283 |
| 3,568,675 | 3/1971 | Harvey | 128/275 |
| 3,901,401 | 8/1975 | Lynn et al. | 215/317 |
| 3,918,131 | 11/1975 | Ausnit | 24/201 C |
| 4,250,882 | 2/1981 | Adair | 128/275 |
| 4,275,732 | 6/1981 | Gereg | 128/276 |

Primary Examiner—C. Fred Rosenbaum
Assistant Examiner—J. L. Kroter
Attorney, Agent, or Firm—Tilton, Fallon, Lungmus

[57] ABSTRACT

A wound drainage device in the form of a flexible pouch having top and bottom walls and having pleated side walls that allow the top wall to be lifted a limited distance without transmitting appreciable lifting or tensioning forces to the bottom wall when the bottom wall is surgically apertured and secured about a wound site. The top wall includes an access opening having a flanged locking ring of flexible plastic extending thereabout. A removable closure cap is attached to the access opening, the cap having a flat rim of flexible plastic with circumferential locking ribs releasably and sealingly engaging a series of mating ribs provided by the flanged portion of the ring.

1 Claim, 6 Drawing Figures

WOUND DRAINAGE DEVICE WITH RESEALABLE ACCESS CAP

BACKGROUND AND SUMMARY

U.S. Pat. No. Re. 29,319 discloses a drainage system for draining fluids from a wound while at the same time permitting observation of and access to that wound. A commercially-available version of such a system is also shown and described in a technical bulletin entitled "Hollister Draining-Wound Management System," published by Hollister Incorporated, Libertyville, Illinois. Such a system includes a drainable pouch having an apertured wall provided with an annular adhesive patch for securing the pouch to a patient in an area surrounding the wound site. The opposite wall of the pouch is provided with an access opening, and a transparent cap is adhesively secured to the pouch about that opening. When access to the wound is required for surgical examination, drain adjustment, wound treatment, or any other reason, the pressure-sensitive adhesive seal between the cap and pouch is broken and the cap is temporarily removed.

The adhesive attachment of the access cap to the pouch is generally effective but is subject to three inherent shortcomings. If reclosure is desired, care must be exercised to avoid contacting the adhesive surfaces with any liquids. Such avoidance may be difficult because of drainage fluids that have passed through the pouch leaving residual amounts clinging to the inner surfaces of the pouch and cap in the vicinity of the adhesive seal. Secondly, a surgeon, nurse, or other attendant must be careful in replacing the cap to avoid pressing the cap firmly against the wall of the bag overlying or surrounding the wound site since even moderate pressure may cause intense pain to the patient. The exercise of judgment is required because limited pressure is necessary in order to adhesively reseal the cap; if too little force is applied, an imperfect seal may be formed and leakage may result. Third, there is always a risk that following its removal, such a cap may be temporarily misplaced or even dropped, resulting in contamination of the cap and necessitating its replacement by a fresh cap which may not always be readily available.

While mechanical seals between ribbed plastic parts are known and have been used for ostomy appliances, such mechanical seals have not been considered suitable for draining wound management systems because of the forces required to join the ribbed sealing elements. Such forces are considerably greater than those needed to create a pressure-sensitive adhesive seal and, hence, would be even more objectionable if applied to the immediate vicinity of the wound. Therefore, although the adhesive mounting of an access cap is not without some objections, no satisfactory substitute for use in a draining wound system has heretofore been known.

This invention is therefore concerned with a wound drainage system having an access cap that is capable of being positively and effectively resealed despite the presence of liquid along the sealing surfaces, and that may be easily and quickly resealed without applying any pressure to the patient in the area of the wound. A further object is to provide a device having sealing means for the access cap that is capable of repeated opening and closing of the cap without deterioration in sealing effectiveness. A still further object is to provide a wound drainage device having an access cap with mechanical sealing means operated by squeezing together the cap and a flanged ring provided by the pouch about its access opening, such squeezing force being applied by the fingers of each hand without the application or transmission of forces to the wound area. It is also an object to provide a pouch that allows and facilitates the closure of an access cap by the application of such squeezing forces without risk of injury or discomfort to the patient. An additional object is to provide an access cap that is permanently attached to the pouch so that it remains readily available when in open position, is less likely to become contaminated because it cannot be misplaced or dropped, and tends to be guided by its connecting straps into a position for resealing when closure is desired.

Briefly, the wound drainage device takes the form of a pouch of flexible fluid (liquid and odor) impermeable plastic film having top, bottom, and side walls, the side walls being accordion-pleated and providing low resistance to unfolding when the top wall is lifted away from the bottom wall. In the embodiment illustrated, the bottom wall has an enlarged aperture with a flexible barrier panel of gas-permeable liquid-resistant material sealed across the aperture and projecting outwardly therefrom. The barrier panel has pressure-sensitive adhesive along its undersurface so that the panel may be secured to a patient about the wound site after the doctor, nurse, or attendant has cut an opening in the panel conforming generally with the outline of the wound.

The top wall of the pouch is provided with an access opening in general alignment with the enlarged aperture in the bottom wall. A flat plastic ring having a flanged periphery is secured to the top wall about the opening and is provided with a series of circumferential ribs projecting upwardly from the flange thereof. A closure cap is provided with a flat plastic rim having depending circumferential ribs capable of releasably and sealingly interlocking with the upstanding ribs of the ring when the rim and ring are squeezed together.

To seal the cap in place, the user first lifts the flanged ring of the pouch's top wall an inch or two above the wound area, such lifting operation causing a partial unfolding of the pleated side walls of the pouch. Because of such pleated construction and flexibility of the plastic film from which the pouch is formed, such a lifting operation may be carried out without transmitting any appreciable forces to the patient in the vicinity of the wound. With the flanged ring thus raised above and wound site, the user simply urges the thin flexible rim of the closure into mechanical sealing engagement with the flanged ring.

The flatness of the ring and closure rim, the arrangement of concentric locking ribs and grooves, and the flexibility or bendability of the plastic material from which such parts are made all contribute towards providing a highly-effective liquid-tight closure that can be easily and repeatedly opened and resealed and yet, at the same time, is highly resistant to unintentional or accidental opening. The interlock is capable of withstanding distortions caused by expansion of the pouch as it is filled, or by any other forces generated during normal use of the drainage device, without risk of separation and leakage. Tabs projecting from the peripheral edges of the ring and rim may be easily gripped and urged apart to initiate opening of the closure and, when fully opened, the cap nevertheless remains connected to the flanged ring of the pouch by means of integrally-formed connecting straps extending between the two.

Other features, objects, and advantages of the invention will become apparent from the specification and drawings.

DRAWINGS

DETAILED DESCRIPTION

Figure 1:
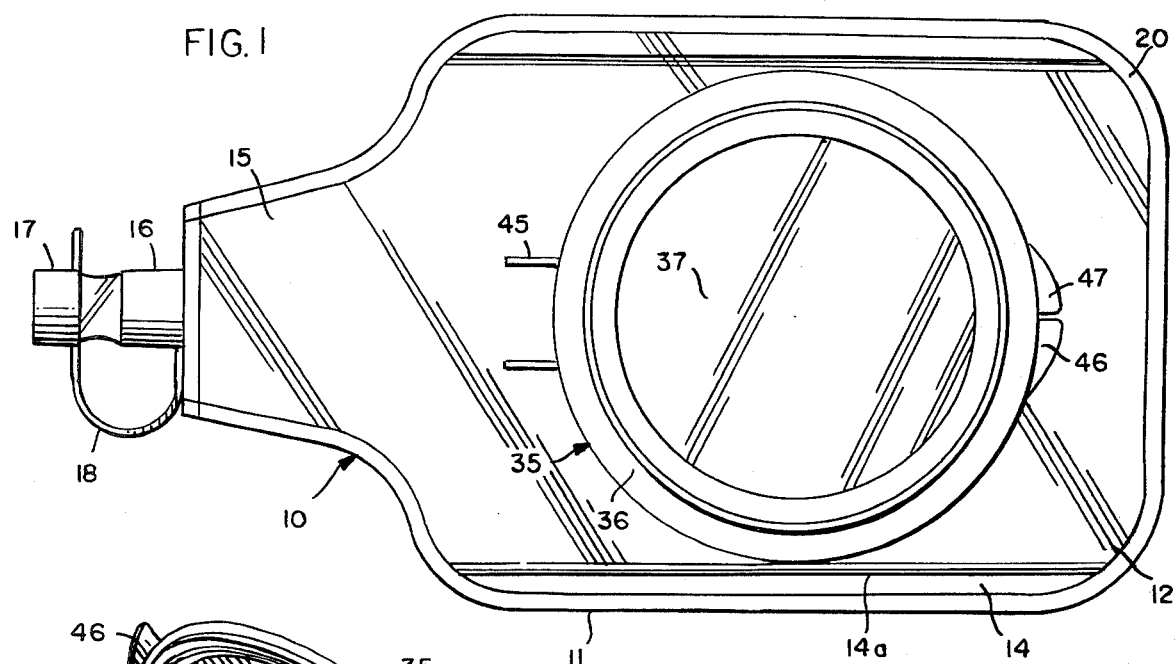
FIG. 1 is a top plan view of a drainage device embodying the invention.

The wound drainage device is generally designated in the drawings by the numeral 10 and includes a pouch 11 having a top wall 12, bottom wall 13, and accordion-pleated side wall 14. The terms "top," "bottom," and "side" are used here to describe the parts of the pouch as they would commonly be oriented with the pouch in a normal position of use; however, it is to be understood that depending on the location of the wound and the condition of the patient, the pouch may assume a variety of different positions in use. Furthermore, the term "wound" is used herein to mean not only penetrating wounds but also fistulas and incisions.

As shown in FIG. 1, the pouch is generally rectangular in outline with a neck portion 15 at one end leading to a drainage tube and cap 16 and 17. An integral strap 18 joins the cap 17 to the tube 16. Removal of the cap allows the liquid contents of the pouch to be drained therefrom. In some cases, it may be desirable to connect an elongated flexible drainage line to tube 16, the line leading to a suitable receptacle. Alternatively, tube 16 and cap 17 may be eliminated completely and the open end of neck 15 may be closed by a suitable clamping device such as the clamp shown and described in U.S. Pat. No. 3,523,534.

Figure 3:
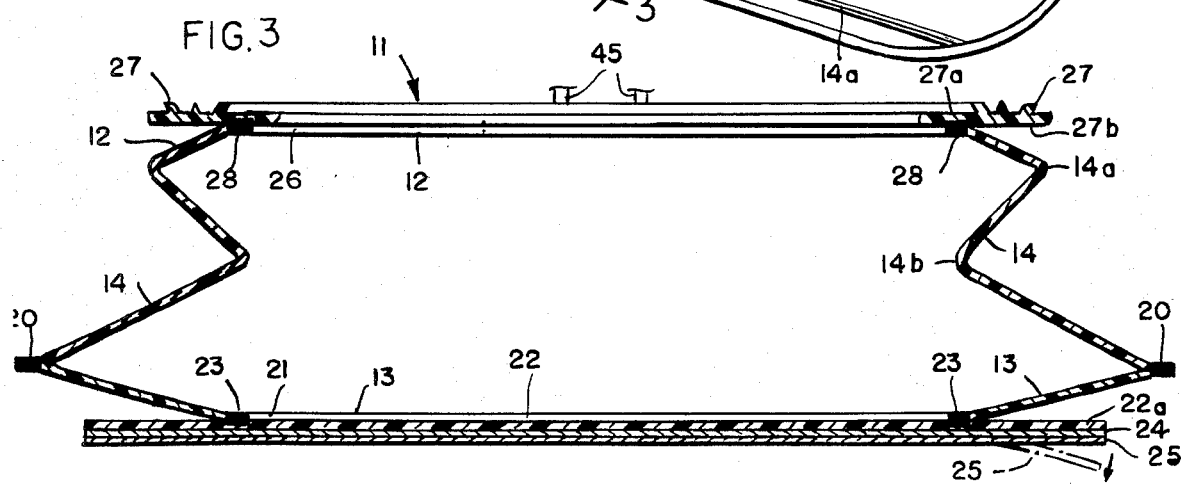
FIG. 3 is a somewhat schematic cross sectional view taken generally along line 3—3 of FIG. 2 but with the top wall of the pouch in raised condition and with background structure omitted for clarity of illustration.

The side walls 14 extend along opposite longitudinal sides of the pouch and, as illustrated most clearly in FIG. 3, are formed as folded extensions of top wall 12. The straight folds 14a and 14b are parallel to each other and preferably to the corresponding folds along the opposite side of the pouch. The outline of the bag is defined by the periphery of bottom wall 13 and that periphery is heat sealed to the top and side walls along a perimetric heat seal zone represented in the drawings by numeral 20.

The walls of the pouch may be formed of any highly flexible liquid-impermeable film or sheet material that has sufficient strength and durability to meet the needs of a liquid-retaining drainage pouch. Polyolefin films, or laminates of polyolefin and other polymeric films providing gas (and odor) barrier properties as well as water barrier characteristics, are believed particularly suitable, but other well-known plastic and plastic laminates may be used. As an example, highly effective results have been obtained by fabricating the top and side walls from a laminate of polyethylene and vinylidene chloride and the bottom wall from a laminate of polyethylene and ethyl vinyl acetate. Such thermoplastics provide sufficient strength, flexibility, and impermeability, and also allow the walls to be joined to each other and to other elements by heat-sealing procedures.

The bottom wall 13 is provided with an enlarged and preferably circular aperture or opening 21 and a flexible barrier panel 22 of liquid-resistant but preferably gas-permeable material is secured to the bottom wall about the edge of the aperture. As shown in FIG. 3, the panel 22 is substantially larger than aperture 21 and has an apron or border portion 22a that projects freely outwardly beneath bottom wall 13. Particularly effective results have been achieved by forming the barrier panel from a non-woven fabric-reinforced ethylene-vinyl acetate copolymer because of its superior fluid barrier and vapor diffusion properties. Such a thermoplastic composition permits the barrier panel to be joined to the bottom wall by heat sealing along heat-seal line 23. However, any of a variety of other thermoplastic materials may be used, especially in applications where vapor transmission properties may be considered less important. Alternatively, where breathability is deemed important and limited moisture transmission can be tolerated, the panel 22 may be formed of non-woven microporous sheet material of rayon or paper, such as the porous non-woven fabric available from Minnesota Mining & Manufacturing Company, Minneapolis, Minnesota, under the brand name "Micropore," or the microporous fabric available as "Scanpore" from Norgesplaster, distributed in the United States by C. R. Bard, Murray Hill, New Jersey.

The underside of the barrier panel 22 is coated with a layer 24 of a surgical, hypo-allergenic pressure-sensitive adhesive. Such adhesives are well known and are commonly acrylic-based. The pressure-sensitive adhesive coating may be covered by a silicone-coated release paper backing 25 that may be peeled away to expose the adhesive layer when the pouch is to be secured to a patient about a wound site.

Figure 5:
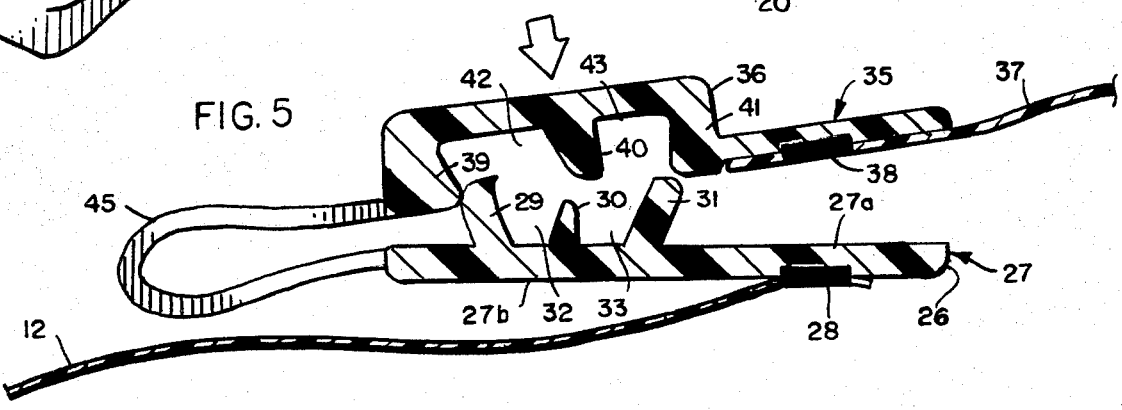
FIG. 5 is an enlarged fragmentary vertical sectional view taken along line 5—5 of FIG. 4 and showing the relationship of the cap rim and flanged ring as the parts are urged together.

Top wall 12 is provided with an opening 26 disposed above aperture 21 in the bottom wall. The opening is preferably circular and approximately the same size as the bottom aperture. A flat, flexible, thermoplastic ring 27 is secured directly to the top wall about opening 26. Referring to FIGS. 3 and 5, it will be noted that the ring 27 has an inner portion 27a, the underside of which is heat sealed at 28 to top wall 12, and an outer flange portion 27b that projects outwardly a substantial distance beyond heat seal 28. The flange has a plurality of upwardly-projecting and circumferentially-extending flexible ribs 29-31, such ribs being separated by concentric grooves or channels 32, 33.

Figure 6:
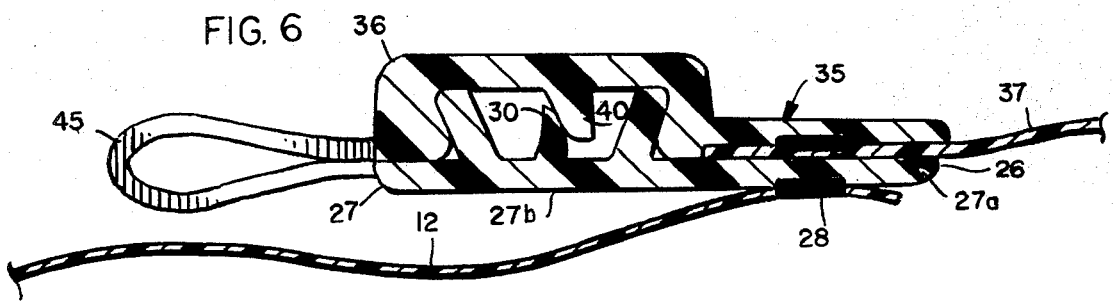
FIG. 6 is a sectional view similar to FIG. 5 but showing the relationship of parts when the access cap is fully closed.

Access cap 35 takes the form of a flat annular rim 36 and a transparent central panel 37. The central panel, which may be formed of a laminate of vinylidene chloride, polyethyene, and ethyl vinyl acetate, or any other suitable thermoplastic material or materials, is heat sealed to the rim along heat seal line 38 (FIG. 5). The rim 36 has dimensions similar to those of ring 27. Depending concentric ribs 39-41 define channels 42 and 43 for receiving the flexible ribs 29-31 of ring 27. In the construction shown, ribs 29 and 31 slope outwardly and inwardly, respectively and, when received within channels 42 and 43, serve primarily to hold the rim 36 and ring 27 together. A liquid-tight seal is achieved primarily by the interaction of central ribs 30 and 40, with smaller rib 30 being cammed or flexed into tight sealing engagement with the sloping surface of rib 40 when rim 36 and ring 27 are locked together (FIG. 6).

The flatness of rim 36 and ring 27 is important because it allows flexing of the two elements when they are connected without allowing independent twisting action that might result in inadvertent or unintentional separation of such parts. The relatively flat construction also permits the use of softer or more pliable materials, thus promoting greater patient comfort and ease of attachment and detachment of the cap. While a variety of materials having such properties might be used, a polyolefin such as low density polyethylene is believed particularly suitable. The central panel 37 of the access cap may be formed of any flexible transparent plastic having adequate barrier properties and capable of being heat sealed to rim 36. For example, a laminate of ethyl vinyl acetate and vinylidene chloride has been found suitable.

Straps 45 join the closure cap to the flanged ring 27. In the embodiment shown, two such straps are provided. Ideally, the connecting straps 45, ring 27, and rim 36 are all integrally formed in the same molding operation.

Tabs 46 and 47 project outwardly from the rim 36 and ring 27 at points generally diametrically opposite from hinge straps 45 and, like the hinge straps are formed as integral parts of the rim and ring. Such tabs are disposed in side-by-side relation when the access cap is closed (FIG. 1), and provide means for gripping the parts to initiate separtion when unsealing of the cap is desired.

Figure 2:
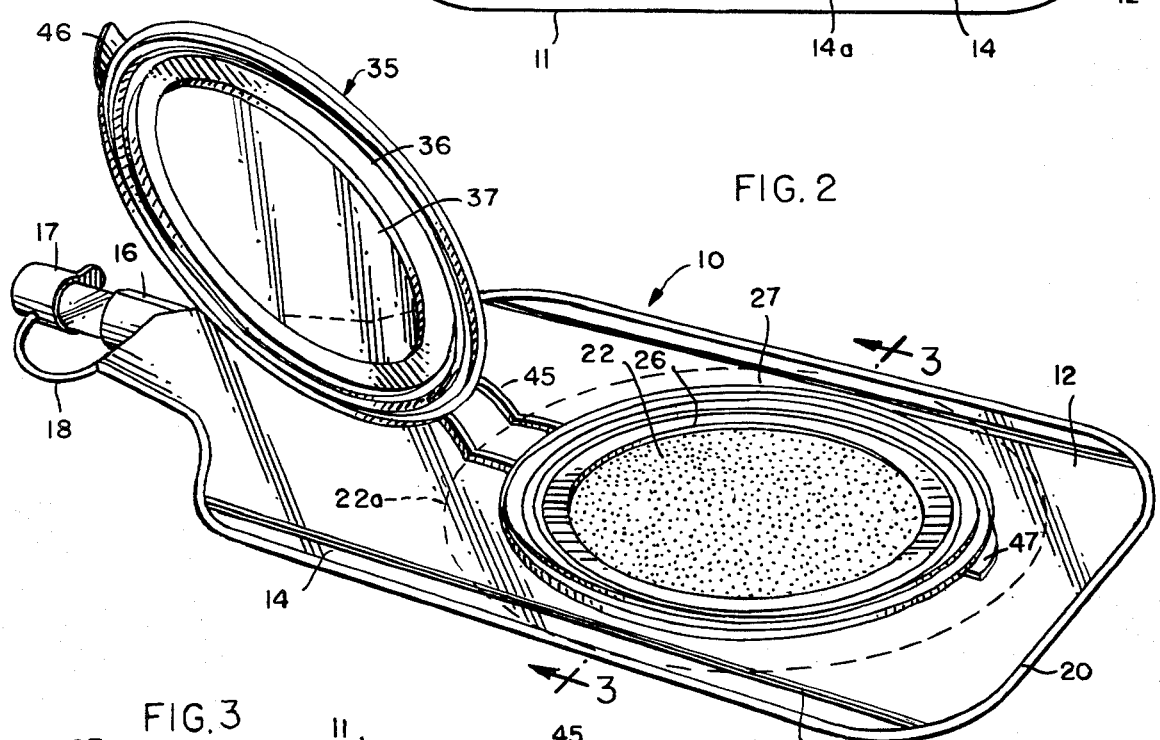
FIG. 2 is a perspective view of the device with the access cap in open position.

When the device is to be applied about a wound site, a user first swings the access cap 35 into open position (FIG. 2) and cuts an opening in barrier panel 22 that follows the general outline of, and is somewhat larger than, the patient's wound. The backing sheet 25 is then stripped away and the panel 22 is adhesively secured to the patient about the wound, with the cut opening of the panel in register with the patient's wound. The wide border portion or flange 22a of the panel provides a substantial area of adhesive attachment to the patient and, if desired, that attachment may be extended and reinforced by applying adhesive tape over and beyond the outer limits of that flange. The accessibility of the top surface of the flange or border portion 22a is therefore of importance when additional taping is to be undertaken. Furthermore, although the barrier panel is effectively an extension of bottom wall 13 within the area of aperture 21, the fact that the flexible flange 22a extends outwardly beyond heat seal 23, and is movable to a limited extent independently of the remainder of the pouch, contributes to more effective sealing attachment between the pouch and patient. For example, referring to FIG. 3, it is believed apparent that should the pouch become filled with fluid, the side wall 14 and bottom wall 13 might balloon outwardly without exerting substantial lifting force upon flange 22a and without disrupting the adhesive seal between the flange and the patient.

In some cases it may be considered desirable to interpose a resilient sealing ring of karaya or similar material between the underside of panel 22 and the patient. Such a karaya blanket is often used to help protect the skin from excoriating fluids. Reference may be had to U.S. Pat. No. Re. 29,319 and U.S. Pat. No. 3,302,647 for further information concerning karaya sealing pads and their formulations.

Figure 4:
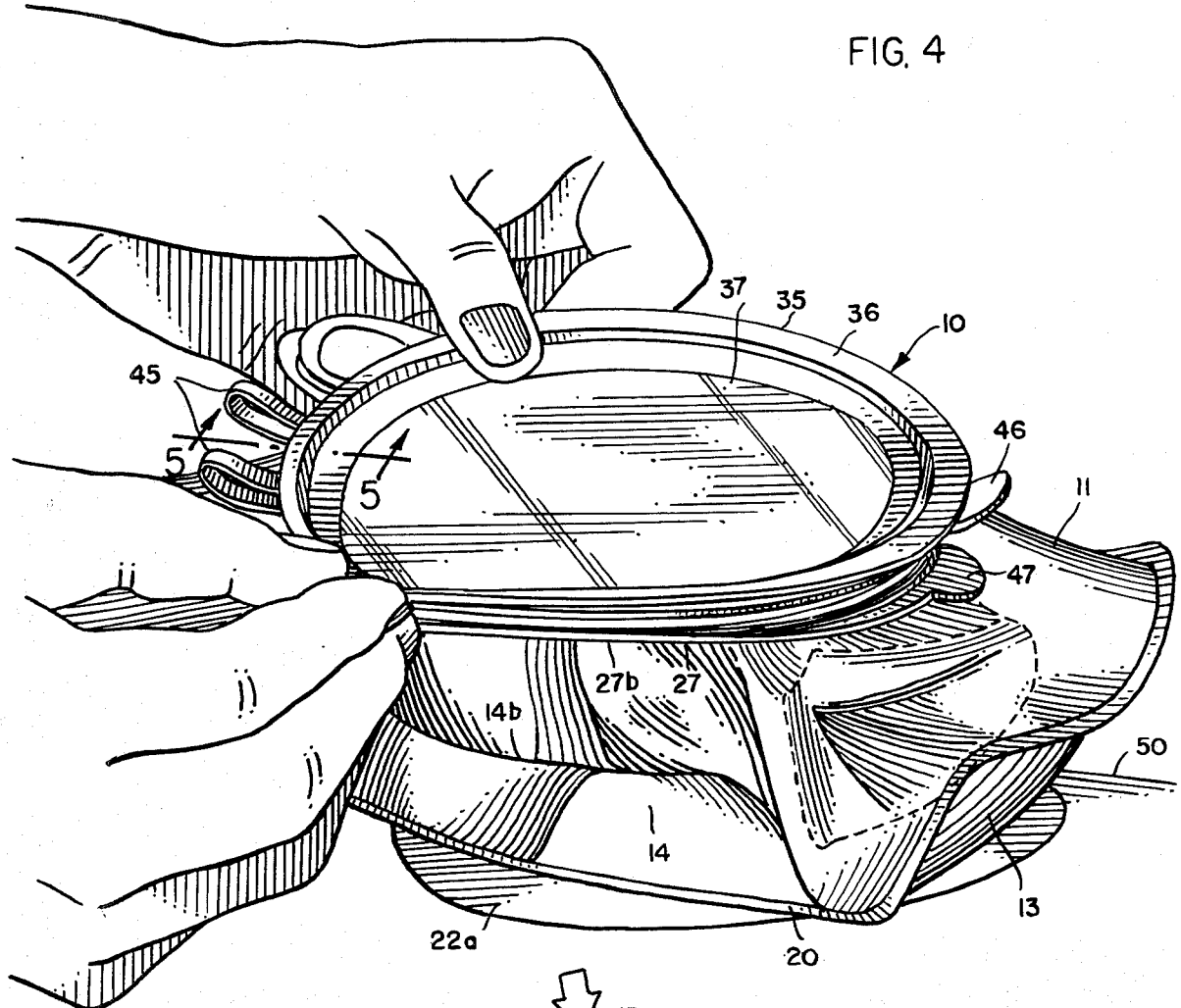
FIG. 4 is a perspective view showing the procedure for sealing the access cap to the flanged pouch ring.

Closure of the pouch is accomplished as depicted in FIG. 4. The user grips the outwardly-projecting flange 27b of ring 27 and lifts the ring away from the patient 50. Such lifting action causes a partial unfolding of side walls 14 and an inflation of the pouch with air entering through opening 26. The access cap is then snapped into sealed position by squeezing the flange 27b of the ring 27 and the ribbed portion of ring 36 together (FIG. 4). The squeezing force may be easily applied using the thumb and index finger of each hand. The squeezing force is applied about the cap and ring until a complete peripheral seal is effected (FIG. 6).

In order to apply such squeezing force as described, and without the risk of injury or discomfort to the patient, it is essential that the user be able to place his (her) fingers beneath the ribbed portion of ring 27 and to urge that portion upwardly into interlocking engagement with the ribbed portion of ring 36. Consequently, the fact that the outer rib-providing flange portion 27b is not directly secured to the top wall 12 of the pouch, and therefore provides an undersurface which is accessible for contact by the operator's fingers, is important for the purpose of providing finger contact for locking the cap in place as well as for lifting the ring away from the patient immediately before the squeezing force is applied. Air entrapped within the pouch after the pouch is closed provides a resilient cushion that tends to protect the wound site from direct contact by the access cap.

Inspection of the wound site, without unsealing the closure cap, is readily accomplished through the clear central panel 37. When access to the wound area is required for drain adjustment or for any other reason, tabs 46 and 47 are urged apart to peel back the closure cap and expose the wound through opeinging 26. The cap remains attached to the ring because of connecting strap 45, and is easily resealed by the pouch-inflating and flange-rim squeezing steps already described.

While in the foregoing an embodiment of the invention has been disclosed in considerable detail for purposes of illustration, it will be understood by those skilled in the art that many of these details may be varied without departing from the spirit and scope of the invention.

I claim:

1. A wound drainage device comprising a pouch of flexible fluid-impermeable plastic material having top, bottom, and side wall means; said side wall means being accordion-pleated and providing low resistance to unfolding when said top wall means is lifted away from said bottom wall means; said bottom wall having an enlarged aperture therein and having a flexible barrier panel of gas-permeable liquid-resistant material sealed across said aperture; adhesive means along the bottom wall means for securing said barrier panel about a wound site after an opening to encompass the wound is formed in said panel; said top wall means having an access opening therein overlying said aperture; a flat ring of flexible plastic material circumferentially secured to the outside upper surface of said top wall means about said opening and provided with a plurality of angularly upstanding circumferentially-extending concentric locking ribs; a removable closure cap for said access opening; said cap including a flat rim of flexible plastic material having a plurality of angularly depending circumferentially-extending locking ribs for releasably and sealingly interlocking with the ribs of said ring when said rim and ring are squeezed together; said ring including an inner portion sealed to said top wall means and a flat outer flange portion unsecured to said top wall means; said angularly upstanding ribs of said ring being provided in the upper surface of said flange portion; and connecting means hingedly connecting said rim of said cap to said flange of said ring for retaining said cap and pouch together when the ribs of said rim and ring are unlocked.

* * * * *